United States Patent [19]

MacLeod

[11] Patent Number: 5,580,877
[45] Date of Patent: Dec. 3, 1996

[54] PYRAZOLO-QUINOLINE DERIVATIVES FOR TREATING CEREBRAL ISCHEMIA

[75] Inventor: Angus M. MacLeod, Bishops Stortford, United Kingdom

[73] Assignee: Merck Sharp & Dohme Ltd., Hoddesdon, United Kingdom

[21] Appl. No.: 427,551

[22] Filed: Apr. 24, 1995

[30] Foreign Application Priority Data

Apr. 25, 1994 [GB] United Kingdom .................. 9408160
Jun. 15, 1994 [GB] United Kingdom .................. 9411953
Dec. 9, 1994 [GB] United Kingdom .................. 9425035

[51] Int. Cl.⁶ .......................... A61K 31/44; C07D 471/04
[52] U.S. Cl. ............................................. 514/292; 546/82
[58] Field of Search ............................... 546/82; 514/292

[56] References Cited

U.S. PATENT DOCUMENTS 5,071,859  12/1991  Knudsen .................................. 514/326
5,399,696   3/1995  Arnold .................................... 546/147

OTHER PUBLICATIONS

Helv. Chim. Acta, (1928), vol. 11, p. 242.
Nagarajan et al. "Condensed Heterotricyles: Synthesis of pyrazolo[3,4–c]quinoline derivatives", Indian Jour. of Chem. vol. 31B, 1992, pp. 316–321.
Petracek FJ. in "Principles of Psychopharmacology" W.G. Clark & J. del Giudance eds. (1970) Academic Press NY. pp. 166–167.

*Primary Examiner*—Ceila Chang
*Assistant Examiner*—Evelyn Huang
*Attorney, Agent, or Firm*—Robert J. North; Melvin Winokur

[57] ABSTRACT

A class of 3,5-dihydro-1H-pyrazolo[3,4-c]quinoline-1, 4(2H)-dione derivatives, substituted in the 2-position by an optionally substituted phenyl moiety, are selective non-competitive antagonists of NMDA receptors and/or are antagonists of AMPA receptors, and are therefore of utility in the treatment and/or prevention of conditions, such as neurodegenerative disorders, convulsions or schizophrenia, which require the administration of an NMDA and/or AMPA antagonist.

11 Claims, No Drawings

PYRAZOLO-QUINOLINE DERIVATIVES FOR TREATING CEREBRAL ISCHEMIA

This invention relates to a class of 3,5-dihydro-1H-pyrazolo[3,4-c]quinoline-1,4(2H)-dione derivatives which are substituted in the 2-position by an optionally substituted phenyl moiety. These compounds are selective non-competitive antagonists of N-methyl-Disparate (NMDA) receptors. More particularly, the class of compounds provided by the present invention are ligands for the strychnine insensitive glycine modulatory site of the NMDA receptor and are therefore useful in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-ponto-cerebellar atrophy, anoxia such as from drowning, spinal cord and head injury, and poisoning by exogenous and endogenous NMDA receptor agonists and neurotoxins, including environmental neurotoxins.

By virtue of their NMDA receptor antagonist properties, the compounds according to the present invention are also useful as anticonvulsant and antiemetic agents, as well as being of value in the prevention or reduction of dependence on dependence-inducing agents such as narcotics.

NMDA receptor antagonists have recently been shown to possess analgesic (see, for example, Dickenson and Aydar, *Neuroscience Lett*, 1991, 12 1,263; Murray et al., *Pain*, 1991, 44, 179; and Woolf and Thompson, *Pain*, 1991, 44, 293), antidepressant (see, for example, Trullas and Skolnick, *Eur. J. Pharmacol.*, 1990, 185, 1) and anxiolytic (see, for example, Kehne et al., *Eur. J. Pharmacol.*, 1991, 193,283) effects, and the compounds of the present invention may accordingly be useful in the management of pain, depression and anxiety.

The association of NMDA receptor antagonists with regulation of the nigrostriated dopaminergic system has recently been reported (see, for example, Werling et al., *J. Pharmacol. Exp. Ther.*, 1990, 255., 40; Graham et ed., *Life Sciences*, 1990, 47, PL-41; and Turski et ed., *Nature (London)*, 1991, 349, 414). This suggests that the compounds of the present invention may thus be of assistance in the prevention and/or treatment of disorders of the dopaminergic system such as schizophrenia and Parkinson's disease.

It has also been reported recently (see Lauritzen et al., *Journal of Cerebral Blood Flow and Metabolism*, 199 1, vol. 11, suppl. 2, Abstract XV-4) that NMDA receptor antagonists block cortical spreading depression (CSD), which may thus be of clinical importance since CSD is a possible mechanism of migraine. The class of substituted 2-amino-4-phosphonomethyledk-3-ene carboxylic acids and esters described in EP-A0420806, which are stated to be selective NMDA antagonists, are alleged thereby to be of potential utility in the treatment of inter alia migraine.

Excitatory amino acid receptor antagonists, including inter alia antagonists of NMDA receptors, are alleged in EP-A-0432994 to be of use in suppressing emesis.

Recent reports in the literature have also suggested a link between the neurotoxicity of certain viruses and the deleterious effects of these viruses on an organism caused by the potentiation of neurotransmission via excitatory amino acid receptors. By virtue of their activity as antagonists of NMDA receptors, therefore, the compounds of the present invention may be effective in controlling the manifestations of neurovired diseases such as measles, rabies, tetanus (cf. Bagetta et ed., Br. *J. Pharmacol.*, 1990, 10 1,776) and AIDS (cf. Lipton et al., *Society for Neuroscience Abstracts*, 1990, 16, 128.11).

NMDA antagonists have, moreover, been shown to have an effect on the neuroendocrine system (see, for example, van den Pol et al., Science, 1990, 250, 1276; and Urbanski, *Endocrinology*, 1990, 127, 2223), and the compounds of this invention may therefore also be effective in the control of seasonal breeding in mammals.

In addition, certain compounds of the invention are antagonists of 2-amino-3-hydroxy-5-methyl-4-isoxazolepropionic acid (AMPA) receptors, also known as quisqualate receptors. An excitatory amino acid projection from the prefrontal cortex to the nucleus accumbens (a particular region of the forebrain possessing dopamine-sensitive neurones) is well known to exist (see, for example, *J. Neurochem.*, 1985, 45, 477). It is also well known that dopaminergic transmission in the striatum is modulated by glutamate (see, for example, *Neurochem. Int.*, 1983, 5, 479), as also is the hyperactivity associated with presynaptic stimulation of the dopamine system by AMPA in the nucleus accumbens (cf. *Life Sci.*, 1981, 28, 1597). Compounds which are antagonists of AMPA receptors are therefore of value as neuroleptic agents.

The preparation of the specific compound 3,5-dihydro-2-phenyl-1H-pyrazolo[3,4-c]quinoline-1,4(2H)-dione is described both in *Helv. Chim. Acta*, 1928, 11,242; and in *Ind. J. Chem.*, 1992, 31B, 316. In neither of these publications, however, is any pharmaceutical utility ascribed to this compound. Moreover, in neither of these publications is there any suggestion that the compounds described therein would be of assistance in solving the problem of providing an effective agent for the treatment and/or prevention of conditions requiting the administration of an antagonist of NMDA and/or AMPA receptors.

The present invention accordingly provides a pharmaceutical composition comprising a compound of formula IA or a pharmaceutically acceptable salt thereof or a prodrug thereof:

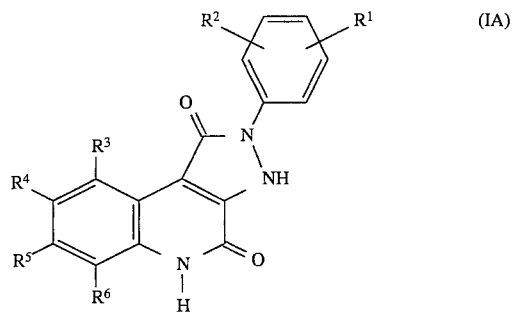

(IA)

wherein $R^1$ and $R^2$ independently represent hydrogen, hydrocarbon, a heterocyclic group, halogen, cyano, trifluoromethyl, nitro, —$OR^1$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$; or $R^1$ and $R^2$ together represent the residue of a carboxylic or heterocyclic ring;

$R^3$, $R^4$, $R^5$ and $R^6$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$; and $R^a$ and $R^b$ independently represent hydrogen, hydrocarbon or a heterocyclic group;

in association with one or more pharmaceutically acceptable carriers and/or excipients.

The invention also provides a compound of formula IA as defined above or a pharmaceutically acceptable salt thereof or a prodrug thereof for use in therapy.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$cycloalkyl, $C_{3-7}$ cycloalkyl($C_{1-6}$)alkyl, aryl, aryl($C_{1-6}$)alkyl, aryl($C_{2-6}$)alkenyl and aryl($C_{2-6}$)alkynyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Suitable aryl groups include phenyl and naphthyl groups.

A particular aryl($C_{1-6}$)alkyl group is benzyl.

A particular aryl($C_{2-6}$)alkenyl group is phenylethenyl.

A particular aryl($C_{2-6}$)alkynyl group is phenylethynyl.

Suitable heterocycloalkyl groups include piperidyl, piperazinyl and morpholinyl groups.

A particular heterocycloalkyl($C_{1-6}$)alkyl group is morpholinylethyl.

Suitable heteroaryl groups include pyridyl, quinolyl, isoquinolyl, pyridazinyl, pyrimidinyl, pyrazinyl, pyrrolyl, indolyl, pyranyl, furyl, benzofuryl, thienyl, benzthienyl, imidazolyl, oxadiazolyl and thiadiazolyl groups. Particular heteroaryl groups are pyridyl, pyrrolyl, indolyl, furyl, benzofuryl, thienyl, benzthienyl and oxadiazolyl.

Particular heteroaryl($C_{1-6}$)alkyl groups include pyridylmethyl, pyrrolylmethyl, indolylmethyl, furylmethyl and thienylmethyl.

Where $R^1$ and $R^2$ together represent the residue of a carboxylic or heterocyclic ring, the ring may be saturated or unsaturated. The ring may suitably be a 4- to 9-membered ring, but will preferably be a 5- or 6-membered ring. Where $R^1$ and $R^2$ together represent the residue of a heterocyclic ring, this ring may contain up to four heteroatoms selected from oxygen, nitrogen and sulphur. Suitable carboxylic rings of which $R^1$ and $R^2$ together represent the residue include cyclohexane, cyclohexene, cyclohexadiene and benzene rings. Suitable heterocyclic rings of which $R^1$ and $R^2$ together represent the residue include dioxolane, dioxane, pyridine, furan, thiophene, pyrrole, thiazole and thiadiazole rings.

The hydrocarbon and heterocyclic groups, as well as the carboxylic or heterocyclic ring completed by $R^1$ and $R^2$, may in turn be optionally substituted by one or more groups selected from ($C_{1-6}$)alkyl, adamantyl, phenyl, halogen, $C_{1-6}$ haloalkyl, morpholinyl($C_{1-6}$)alkyl, trifluoromethyl, hydroxy, $C_{1-6}$ alkoxy, $C_{1-6}$ alkoxy($C_{1-6}$)alkyl, $C_{1-6}$ alkoxy($C_{1-6}$)alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, amino, mono- or di($C_{1-6}$)alkylamino, $C_{2-6}$ alkylcarbonylamino and $C_{2-6}$ alkoxycarbonylamino.

The term "halogen" as used herein includes fluorine, chlorine, bromine and iodine, especially chlorine.

Suitable values for the substituents $R^1$ and $R^2$ include $C_{1-6}$ alkyl, aryl, aryl($C_{1-6}$)alkyl, aryl($C_{2-6}$)alkenyl, aryl($C_{2-6}$)alkynyl, heteroaryl($C_{1-6}$)alkyl, $C_{1-6}$ alkoxy, $C_{2-6}$ alkenyloxy, aryloxy, aryl($C_{1-6}$)alkoxy, heteroaryloxy, arylthio, arylsulphonyl, arylamino, aryl($C_{1-6}$)alkylamino, di($C_{1-6}$)alkylamino, arylcarbonylamino, arylcarbonyl or heteroarylcarbonyl, any of which groups may be optionally substituted; and hydrogen, halogen, trifluoromethyl or nitro. Examples of additional substituents on the groups $R^1$ and/or $R^2$ include $C_{1-6}$ alkyl, morpholinyl($C_{1-6}$)alkyl, hydroxy, $C_{1-6}$ alkoxy, $C_{1-6}$ alkoxy($C_{1-6}$)alkyl, $C_{1-6}$ alkoxy($C_{1-6}$)alkoxy, $C_{1-6}$ alkylthio and di($C_{1-6}$)alkylamino.

Particular values for the substituents $R^1$ and $R^2$ include hydrogen, methyl, phenyl, benzyl, methoxymethyl-benzyl, morpholinylethyl-benzyl, hydroxybenzyl, methoxybenzyl, methoxymethoxy-benzyl, methylthio-benzyl, phenylethenyl, phenylethynyl, thienylmethyl, pyrrolylmethyl, indolylmethyl, fluoro, chloro, bromo, iodo, trifluoromethyl, nitro, methoxy, ethoxy, allyloxy, methyl-allyloxy, phenoxy, methyl-phenoxy, methoxy-phenoxy, dimethylamino-phenoxy, benzyloxy, furyloxy, thienyloxy, pyriclyloxy, phenylthio, phenylsulphonyl, phenylamino, benzylamino, dimethylamino, phenylcarbonylamino, phenylcarbonyl, furylcarbonyl and thienylcarbonyl.

Suitably, one or both of $R^1$ and $R^2$ represent hydrogen.

Where $R^1$ and $R^2$ together represent the residue of a carboxylic or heterocyclic ring, this may be, in particular, a dioxolane or optionally substituted benzene ring.

The benzo moiety of the fused tricyclic ring system shown in formula IA above may be substituted or unsubstituted. Particular substituents include halogen, cyano, trifluoromethyl, nitro, hydroxy, amino, carboxy, $C_{1-6}$ alkyl, $C_{2-6}$ alkenyl, $C_{1-6}$ alkoxy, $C_{1-6}$ alkylthio and $C_{2-7}$ alkoxycarbonyl. Suitably $R^6$ is hydrogen and $R^3$, $R^4$ and $R^5$ independently represent hydrogen, halogen, cyano, trifluoromethyl, nitro, $C_{1-6}$ alkyl or $C_{2-6}$ alkenyl, at least one of $R^3$, $R^4$ and $R^5$ desirably being other than hydrogen. Preferably, $R^4$ and $R^6$ each represents hydrogen and $R^3$ and $R^5$ independently represent hydrogen, cyano, trifluoromethyl, nitro, methyl, ethyl, vinyl or halogen, especially chlorine or iodine. In a particular embodiment, $R^5$ represents hydrogen, cyano, trifluoromethyl, nitro or halogen, especially chlorine; and $R^s$ is hydrogen or ethyl.

Particular pharmaceutical compositions according to the invention contain, as the active ingredient, at least one of the following compounds:
3,5-dihydro-2-phenyl-1H-pyrazolo[3,4-c]quinoline-1, 4(2H)-dione; and pharmaceutically acceptable salts thereof and prodrugs thereof.

Certain compounds falling within the definition of formula IA above are novel. Accordingly, in a still further aspect the present invention provides a compound of formula IB or a salt or prodrug thereof:

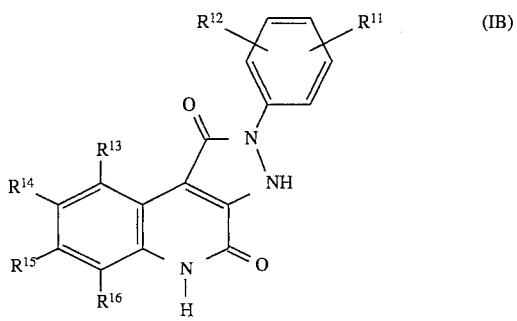 (IB)

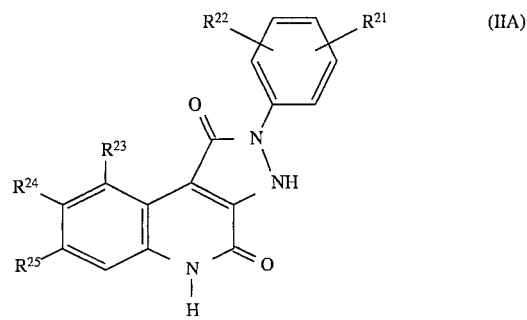 (IIA)

wherein $R^{11}$ and $R^{12}$ independently represent hydrogen, hydrocarbon, a heterocyclic group, halogen, cyano, trifluoromethyl, nitro, —$OR^a$, —$SR^a$, —$SOR^a$, $SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$; or $R^{11}$ and $R^{12}$ together represent the residue of a carboxylic or heterocyclic ring;

$R^{13}$, $R^{14}$, $R^{15}$ and $R^{16}$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^2$ or —$CONR^aR^b$; and $R^a$ and $R^b$ independently represent hydrogen, hydrocarbon or a heterocyclic group;

provided that $R^{11}$, $R^{12}$, $R^{13}$, $R^{14}$, $R^{15}$ and $R^{16}$ are not all simultaneously hydrogen.

Subject to the above proviso, the substituents $R^{11}$ to $R^{16}$ in the compounds of formula IB correspond to the substituents $R^1$ to $R^6$ respectively as defined with reference to the compounds of formula IA.

For use in medicine, the salts of the compounds of formula IB will be pharmaceutically acceptable salts. Other salts may, however, be useful in the preparation of the compounds according to the invention or of their pharmaceutically acceptable salts.

Suitable pharmaceutically acceptable salts of the compounds of formulae IA and IB above include alkali metal salts, e.g. lithium, sodium or potassium salts; alkaline earth metal salts, e.g. calcium or magnesium salts; and salts formed with suitable organic ligands, e.g. quaternary ammonium salts. Where appropriate, acid addition salts may, for example, be formed by mixing a solution of the compound according to the invention with a solution of a pharmaceutically acceptable acid such as hydrochloric acid, sulphuric acid, fumaric acid, maleic acid, succinic acid, acetic acid, citric acid, tartaric acid, carbonic acid or phosphoric acid.

The present invention includes within its scope prodrugs of the compounds of formulae IA and IB above. In general, such prodrugs will be functional derivatives of the compounds of formulae IA and IB which are readily convertible in vivo into the required compound. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

One sub-class of compounds according to the invention is represented by the compounds of formula IIA and salts and prodrugs thereof:

wherein $R^{21}$ and $R^{22}$ independently represent $C_{1-6}$ alkyl, $C_{2-6}$ alkenyl, $C_{2-6}$ alkynyl, aryl, aryl($C_{1-6}$)alkyl, aryl($C_{2-6}$)alkenyl, aryl($C_{2-6}$)alkynyl, heteroaryl($C_{1-6}$)alkyl, $C_{1-6}$ alkoxy, $C_{2-6}$ alkenyloxy, aryloxy, aryl($C_{1-6}$)alkoxy, heteroaryloxy, $C_{1-6}$ alkylthio, arylthio, arylsulphonyl, arylamino, aryl($C_{1-6}$)alkylamino, di($C_{1-6}$)alkylamino, arylcarbonylamino, arylcarbonyl, heteroarylcarbonyl or $C_{2-7}$ alkoxycarbonyl, any of which groups may be optionally substituted; or hydrogen, halogen, cyano, trifluoromethyl, nitro, hydroxy, amino or carboxy; or $R^{21}$ and $R^{22}$ together represent the residue of a carboxylic or heterocyclic ring;

$R^{23}$ and $R^{24}$ independently represent hydrogen, halogen, cyano, trifluoromethyl, nitro, hydroxy, amino, carboxy, $C_{1-6}$ alkyl, $C_{2-6}$ alkenyl, $C_{1-6}$ alkoxy, $C_{1-6}$ alkylthio or $C_{2-7}$ alkoxycarbonyl; and $R^{25}$ represents halogen, cyano, trifluoromethyl, nitro, hydroxy, amino, carboxy, $C_{1-6}$ alkyl, $C_{2-6}$ alkenyl, $C_{1-6}$ alkoxy, $C_{1-6}$ alkylthio or $C_{2-7}$ alkoxycarbonyl.

Examples of optional substituents on the groups $R^{21}$ and/or $R^{22}$ include $C_{1-6}$ alkyl, morpholinyl($C_{1-6}$)alkyl, hydroxy, $C_{1-6}$ alkoxy, $C_{1-6}$ alkoxy($C_{1-6}$)alkyl, $C_{1-6}$ alkoxy($C_{1-6}$)alkoxy, $C_{1-6}$ alkylthio and di($C_{1-6}$)alkylamino.

Particular values of $R^{21}$ and/or $R^{22}$ with respect to formula IIA include hydrogen, methyl, phenyl, benzyl, methoxymethyl-benzyl, morpholinylethyl-benzyl, hydroxybenzyl, methoxybenzyl, methoxymethoxy-benzyl, methylthiobenzyl, phenylethenyl, phenylethynyl, thienylmethyl, pyrrolylmethyl, indolylmethyl, fluoro, chloro, bromo, iodo, trifluoromethyl, nitro, methoxy, ethoxy, allyloxy, methylallyloxy, phenoxy, methyl-phenoxy, methoxy-phenoxy, dimethylamino-phenoxy, benzyloxy, furyloxy, thienyloxy, pyridyloxy, phenylthio, phenylsulphonyl, phenylamino, benzylamino, dimethylamino, phenylcarbonylamino, phenylcarbonyl, furylcarbonyl and thienylcarbonyl.

Suitably, at least one of $R^{21}$ and $R^{22}$ represents hydrogen. In a particular embodiment, one of $R^{21}$ and $R^{22}$ is hydrogen and the other is hydrogen, chloro, methoxy or phenoxy.

Suitably, $R^{23}$ represents hydrogen, nitro, methyl, ethyl, vinyl or halogen, especially chlorine or iodine. Preferably, $R^{23}$ is hydrogen, ethyl, chlorine or iodine.

Suitably, $R^{24}$ represents hydrogen or chlorine, preferably hydrogen.

Suitably, $R^{25}$ represents cyano, trifluoromethyl, nitro, methyl or halogen, preferably chlorine.

Another sub-class of compounds according to the invention is represented by the compounds of formula IIB and salts and prodrugs thereof:

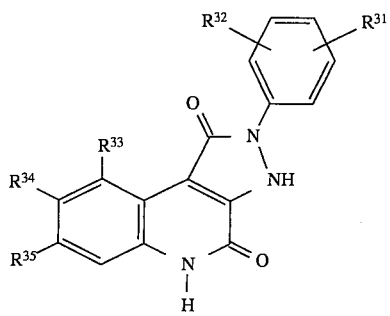

(IIB)

wherein

R³¹ represents C₁₋₆ alkyl, C₂₋₆ alkenyl, C₂₋₆ alkynyl, aryl, aryl(C₁₋₆)alkyl, aryl(C₂₋₆)alkenyl, aryl(C₂₋₆)alkynyl, heteroaryl(C₁₋₆)alkyl, C₁₋₆ alkoxy, C₂₋₆ alkenyloxy, aryloxy, aryl(C₁₋₆)alkoxy, heteroaryloxy, C₁₋₆ alkylthio, arylthio, arylsulphonyl, arylamino, aryl(C₁₋₆)alkylamino, di(C₁₋₆)alkylamino, arylcarbonylamino, arylcarbonyl, heteroarylcarbonyl or C₂₋₇ alkoxycarbonyl, any of which groups may be optionally substituted; or hydrogen, halogen, cyano, trifluoromethyl, nitro, hydroxy, amino or carboxy; and R³² represents C₁₋₆ alkyl, C₂₋₆ alkenyl, C₂₋₆ alkynyl, aryl, aryl(C₁₋₆)alkyl, aryl(C₂₋₆)alkenyl, aryl(C₂₋₆)alkynyl, heteroaryl(C₁₋₆)alkyl, C₁₋₆ alkoxy, C₂₋₆ alkenyloxy, aryloxy, aryl(C₁₋₆)alkoxy, heteroaryloxy, C₁₋₆ alkylthio, arylthio, arylsulphonyl, arylamino, aryl(C₁₋₆)alkylamino, di(C₁₋₆)alkylamino, arylcarbonylamino, arylcarbonyl, heteroarylcarbonyl or C₂₋₇ alkoxycarbonyl, any of which groups may be optionally substituted; or halogen, cyano, trifluoromethyl, nitro, hydroxy, amino or carboxy; or R³¹ and R³² together represent the residue of a carboxylic or heterocyclic ring; and R³³, R³⁴ and R³⁵ independently represent hydrogen, halogen, cyano, trifluoromethyl, nitro, hydroxy, amino, carboxy, C₁₋₆ alkyl, C₂₋₆ alkenyl, C₁₋₆ alkoxy, C₁₋₆ alkylthio or (C₂₋₇ alkoxycarbonyl.

Examples of optional substituents on the groups R³¹ and/or R³² include C₁₋₆ alkyl, morpholinyl(C₁₋₆)alkyl, hydroxy, alkoxy(C₁₋₆)alkyl, C₁₋₆ alkoxy(C₁₋₆)alkoxy, C₁₋₆ alkylthio and di(C₁₋₆)alkylamino.

Particular values of R³¹ and/or R³² with respect to formula IIB include methyl, phenyl, benzyl, methoxymethylbenzyl, morphlinylethylbenzyl, hydroxybenzyl, methoxybenzyl, methoxymethoxy-benzyl, methylthio-benzyl, phenylethenyl, phenylethynyl, thienylmethyl, pyrrolylmethyl, indolylmethyl, fluoro, chloro, bromo, iodo, trifluoromethyl, nitro, methoxy, ethoxy, allyloxy, methyl-allyloxy, phenoxy, methylphenoxy, methoxy-phenoxy, dimethylamino-phenoxy, benzyloxy, furyloxy, thienyloxy, pyridyloxy, phenylthio, phenylsulphonyl, phenylamino, benzylamino, dimethylamino, phenylcarbonylamino, phenylcarbonyl, furylcarbonyl and thienylcarbonyl. In addition, R³¹ may represent hydrogen.

Suitably, R³¹ is hydrogen. In a particular embodiment, R³¹ is hydrogen and R³² is chloro, methoxy or phenoxy.

Suitably, R³³ represents hydrogen, nitro, methyl, ethyl, vinyl or halogen, especially chlorine or iodine. Preferably, R³³ is hydrogen, ethyl, chlorine or iodine.

Suitably, R³⁴ represents hydrogen or chlorine, preferably hydrogen.

Suitably, R³⁵ represents hydrogen, cyano, trifluoromethyl, nitro, methyl or halogen, preferably hydrogen or chlorine.

Specific compounds within the scope of the present invention include:
7-chloro-3,5-dihydro-2-phenyl-1H-pyrazolo[3,4-c]quinoline-1,4(2H)-dione; 2-(2-chlorophenyl)-3,5-dihydro-1H-pyrazolo[3,4-c]quinoline-1,4(2H)-dione; 2-(3-chlorophenyl)-3,5-dihydro-1H-pyrazolo[3,4-c]quinoline-1,4(2H)-dione; 2-(4-chlorophenyl)-3,5-dihydro-1H-pyrazolo[3,4-c]quinoline-1,4(2H)-dione; 3,5-dihydro-2-(4-methoxyphenyl)-1H-pyrazolo[3,4-c]quinoline-1, 4(2H)dione; 7-chloro-3,5-dihydro-2-(4-methoxyphenyl)-1H-pyrazolo[3,4-c]quinoline-1,4(2H)-dione; and salts and prodrugs thereof.

The pharmaceutical compositions according to the invention are preferably in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the tbrmer. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of neurodegeneration, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day. In a particular embodiment, the compounds may be conveniently administered by intravenous infusion.

The compounds of formula IA above, including the novel compounds according to the present invention, may be prepared by a process which comprises reacting a compound of formula III with a compound of formula IV:

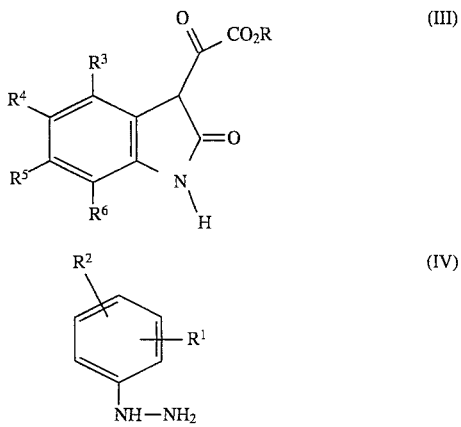

wherein $R^1$, $R^2$, $R^3$, $R^4$, $R^5$ and $R^6$ are as defined above, and R represents $C_{1-6}$ alkyl; in the presence of an acid.

Suitable values for the substituent R include methyl and ethyl, especially ethyl.

The reaction is conveniently effected by heating compounds III and IV together at reflux in acetic acid, which also acts as the solvent.

The starting materials of formula III may conveniently be prepared from a substituted oxindole derivative by a method analogous to that described in *Justus Liebigs Ann. Chem.,* 1924, 436, 113. A general procedure for preparing substituted oxindoles is described in *Synthesis,* 1993, 51.

Where they are not commercially available, the reagents of formula IV may suitably be prepared by standard methods well known from the art.

It will be appreciated that any compound of formula IA initially obtained from the above process may, where appropriate, subsequently be elaborated into a further desired compound of formula IA using techniques known from the art.

Where the above-described process for the preparation of compounds of use in the invention gives rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (-)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides,, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry,* ed. J. F. W. McOmie, Plenum Press, 1973; and T. W. Greene & P. G. M. Wuts, *Protective Groups in Organic Synthesis,* John Wiley & Sons, 1991. The protecting groups may be removed at a convenient subsequent stage using methods known from the art.

The following Examples illustrate the preparation of compounds of use in the invention.

The compounds useful in this invention potently and selectively block responses to NMDA and/or AMPA in a brain slice from rat cortex, and inhibit the binding of agonists and antagonists to the strychnine-insensitive site present on the NMDA receptor and/or AMPA binding to rat forebrain membranes.

CORTICAL SLICE STUDIES

The effects of compounds of use in the invention on responses to NMDA and AMPA can be assessed using the rat cortical slice as described by Wong et al., *Proc. Natl. Acad. Sci. USA,* 1986, 83, 7104. The apparent equilibrium constant ($K_b$b) is calculated from the righthand shift in the NMDA or AMPA concentration-response curves produced by the compound under test. The compounds of the accompanying Examples were tested and were found to possess $K_b$ values in response to NMDA of below 150 µM in each case.

BINDING STUDIES

The ability of test compounds to displace $^3$H-L-689,560 (trans-2-carboxy-5,7-dichloro-4-phenyl-aminocarbonylamino-1,2,3,4-tetrahydroquinoline) binding to the strychnine-insensitive site present on the NMDA receptor of rat forebrain membranes can be determined by the method of Grimwood et al., *Proceedings of The British Pharmacological Society,* Jul. 1991, Abstract C78. The concentration of the compounds of the accompanying Examples required to displace 50% of the specific binding ($IC_{50}$) is below 50 µM in each case.

EXAMPLE 1

3,5-Dihydro-2-phenyl-1H-pyrazolo[3,4-c]quinoline-1, 4(2H)-dione

Ethyl oxindole-3-glyoxylate (220 rag) in glacial acetic acid (2 ml) was heated under reflux for 10 minutes with phenylhydrazine (0.1 ml). The reaction was cooled and the resulting precipitate filtered and crystallised from methanol to give the title compound, mp>260° C.; $^1$H nmr (250 MHz, $d_6$-DMSO) δ5 11.86 (1H, broad s), 8.25 (1H, broad d), 7.86 (2H, d, J=8 Hz), 7.56 (2H, t, J=8 Hz) and 7.22–7.42 (4H, m).

The following examples were prepared by the method of Example 1 using the appropriately substituted phenylhydrazine and oxindole reagents.

EXAMPLE 2

7-Chloro-3,5-dihydro-2-phenyl-1H-pyrazolo[3,4-c]quinoline-1,4(2H)-dione $^1$H nmr (250 MHz, $d_6$-DMSO) 7.30 (1H, dd, J=3 Hz and 12.2 Hz), 7.37–7.43 (2H, m), 7.56 (2H, t, J=8 Hz), 7.84 (2H, d, J=8 Hz) and 8.20 (1H, d, J=8 Hz).

EXAMPLE 3

3,5-Dihydro-2-(2-chlorophenyl)-1H-pyrazolo[3,4-c]quinoline-1,4(2H)-dione $^1$H nmr (250 MHz, $d_6$-DMSO) 7.29–7.41 (3H, m), 7.52–7.77 (4H, m) and 8.16 (1H, bs).

EXAMPLE 4

3,5-Dihydro-2-(3-chlorophenyl)-1H-pyrazolo[3,4-c]quinoline-1,4(2H)-dione $^1$H nmr (360 MHz, $d_6$-DMSO) 7.20–7.44 (4H, m), 7.58 (1H, t, J=8 Hz), 7.86 (1H, d, J=8 Hz), 8.02 (1H, s) and 8.37 (1H, d, J=8 Hz).

EXAMPLE 5

3,5-Dihydro-2-(4-chlorophenyl)-1H-pyrazolo[3,4-c]quinoline-1,4(2H)-dione $^1$H nmr (250 MHz, d$_6$-DMSO) 7.20–7.38 (3H, m), 7.62 (2H, d, J=12.6 Hz), 7.91 (2H, d, J=12.6 Hz) and 8.25 (1H, d, J=10.9 Hz).

EXAMPLE 6

3,5-Dihydro-2-(4-methoxyphenyl)-1H-pyrazolo[3,4-c]quinoline-1,4(2H)-dione $^1$H nmr (250 MHz, d$_6$-DMSO) δ8.21 (1H, broad s,), 7.73 (2H, d, J=9 Hz), 7.31–7.35 (2H, m), 7.12–7.25 (1H, m), 7.11 (2H, d, J=9 Hz), 3.8 (3H, s); MS (ES$^+$) 308 [M+H]$^+$.

EXAMPLE 7

7-Chloro-3,5-dihydro-2-(4-methoxyphenyl)-1H-pyrazolo[3,4-c]quinoline-1,4(2H)-dione $^1$H nmr (250 MHz, d$_6$-DMSO) δ11.46 (1H, broad s), 7.85 (1H, d, J=8.4 Hz), 7.40 (2H, d, J=9.0 Hz), 7.07 (1H, d, J-2 Hz), 6.98 (1H, dd, J=2 Hz and 8.4 Hz), 6.81 (2H, d, J=9.0 Hz), 3.52 (3H, s); MS (ES$^+$) 342/344 [M+H]$^+$.

What is claimed is:

1. A pharmaceutical composition containing, as the active ingredient, at least one of the following compounds: 3,5-dihydro-2-phenyl-1H-pyrazolo[3,4-c]quinoline-1,4(2H)-dione; and pharmaceutically acceptable salts thereof and prodrugs thereof, together with a pharmaceutical carrier.

2. A method for the treatment of neurodegeration resulted from cerebral ischaemia which require the administration of a selective non-competitive antagonist of NMDA receptors, which method comprises administering to a patient in need thereof an effective amount of the compound of claim 1 or a pharmaceutically acceptable salt thereof or a prodrug thereof.

3. A compound represented by Formula IIA and, pharmaceutically acceptable salts and prodrugs thereof:

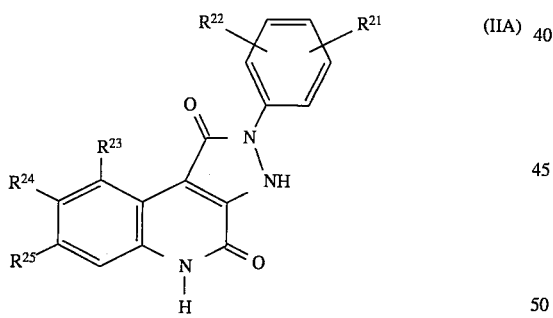

wherein

R$^{21}$ and R$^{22}$ is hydrogen and the other is hydrogen, chloro, methoxy or phenoxy;

R$^{23}$ is hydrogen, ethyl, chloro or iodo;

R$^{24}$ is hydrogen or chloro; and

R$^{25}$ represents cyano, trifluoromethyl, nitro, methyl or halogen.

4. A compound as claimed in claim 3 wherein R$^{25}$ is chloro.

5. A compound represented by Formula IIB and pharmaceutically acceptable salts and prodrugs thereof:

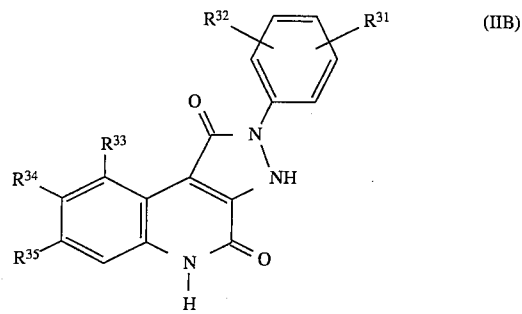

wherein

R$^{31}$ is hydrogen and R$^{32}$ is chloro, methoxy or phenoxy;

R$^{33}$ is hydrogen, ethyl, chloro or iodo;

R$^{34}$ is hydrogen or chloro;

R$^{35}$ represents hydrogen, cyano, trifluoromethyl, nitro, methyl or halogen.

6. A compound as claimed in claim 5 wherein R$^{35}$ is hydrogen or chloro.

7. A compound selected from:

7-chloro-3,5-dihydro-2-phenyl-1H-pyrazolo[3,4-c]quinoline-1,4(2H)-dione;

2-(2-chlorophenyl)-3,5-dihydro-1H-pyrazolo[3,4-c]quinoline-1,4(2H)-dione;

2-(3-chlorophenyl)-3,5-dihydro-1H-pyrazolo[3,4-c]quinoline-1,4(2H)-dione;

3,5-dihydro-2-(4-chlorophenyl)-3,5-dihydro-1H-pyrazolo[3,4-c]quinoline-1,4(2H)-dione;

7-chloro-3,5-dihydro-2-(4-methoxyphenyl)-1H-pyrazolo[3,4-c]quinoline-1,4(2H)-dione;

and pharmaceutically acceptable salts and prodrugs thereof.

8. A pharmaceutical composition comprising a compound as claimed in claim 3 in association with one or more pharmaceutically acceptable carriers and/or excipients.

9. A method for the treatment of neurodegeration resulted from cerebral ischaemia which require the administration of a selective non-competitive antagonist of NMDA receptors, which method comprises administering to a patient in need thereof an effective amount of a compound as claimed in claim 3.

10. A method for the treatment of neurodegeneration resulted from cerebral ischaemia which require the administration of selective non-competitive an antagonist of NMDA receptors, which method comprises administering to a patient in need thereof an effective amount of a compound as claimed in claim 5.

11. A pharmaceutical composition comprising a compound as claimed in claim 5 in association with one or more pharmaceutically acceptable carriers and/or excipients.

* * * * *